US006309836B1

(12) United States Patent
Kwiatkowski

(10) Patent No.: US 6,309,836 B1
(45) Date of Patent: Oct. 30, 2001

(54) COMPOUNDS FOR PROTECTING HYDROXYLS AND METHODS FOR THEIR USE

(76) Inventor: Marek Kwiatkowski, Lövsängarvägen 17, SE-756 52, Uppsala (SE)

(*) Notice: Subject to any disclaimer, the term of this patent is extended or adjusted under 35 U.S.C. 154(b) by 0 days.

(21) Appl. No.: 09/412,171

(22) Filed: Oct. 5, 1999

(51) Int. Cl.⁷ .............................. C12Q 1/68; C12P 19/34; C07H 19/00; C07H 21/02; C07H 21/04

(52) U.S. Cl. .......................... 435/6; 435/91.1; 435/91.2; 536/22.1; 536/23.1; 536/24.3; 536/24.33; 536/25.3

(58) Field of Search ............................ 435/6, 91.1, 91.2; 536/22.1, 23.1, 24.3, 24.33, 25.3

(56) References Cited

U.S. PATENT DOCUMENTS

| | | | |
|---|---|---|---|
| 5,216,134 | 6/1993 | Mukkala et al. | 534/15 |
| 5,252,462 | 10/1993 | Drevin et al. | 435/18 |
| 5,256,535 | 10/1993 | Ylikoski et al. | 435/6 |
| 5,405,746 | 4/1995 | Uhlen | 435/6 |
| 5,858,671 | 1/1999 | Jones | 435/6 |
| 5,871,921 | 2/1999 | Landegren et al. | 435/6 |
| 5,888,778 | 3/1999 | Shuber | 435/91.1 |

FOREIGN PATENT DOCUMENTS

| | | |
|---|---|---|
| WO 96/23807 | 8/1996 | (WO) . |
| WO 98/08857 | 5/1998 | (WO) . |
| WO 98/51698 | 11/1998 | (WO) . |

OTHER PUBLICATIONS

Kahl & Greenburg, "Introducing Structural Diversity in Oligonucleotides via Photolabile, Convertible C5-substituted Necleotides," *J. Am. Chem. Soc.*, 121(4), (1999), pp. 597–604.

Beaucage & Iyer, "Advances in the Synthesis of Oligonucleotides by the Phosphoramidite Approache," *Tetrahedron*, 48(12), pp. 2223–2311.

Beaucage & Iyer, "The Synthesis of Specific Ribonucleotides and Unrelated Phosphorylated Biomolecules by the Phosphoramidite Method," *Tetrahedron*, 49(46), pp. 1044–10488 (1993).

Scaringe et al., "Novel RNA Synthesis Method Using 5'-Osilyl-2'O-orthoester Protecting Groups," *J. Am. Chem. Soc.*, 120:11820–21 (1998).

Hovinen et al., "Synthesis of 3'-0-(ω-Aminoalkoxymethyl) thymidine 5'-Triphosphates, Terminators of DNA synthesis that Enable 3'-Labeling," *J. Chem. Soc. Perkin Trans.* I, pp. 211–217 (1994).

Bruice & Kenyon, "Novel Alkyl Alkanethiolsulfonate Sulfhydryl reagents, Modifications of Derivatives of L–Cysteine," *J. Protein Chem.*, 1(1): 47–58 (1982).

Plettner et al., "A Combinational Approach to Chemical Modification of Subtilisin Bacillus lentus," *Bioorganic & Medicinal Chem.* Lett. 8, pp. 2291–96 (1998).

Sanger et al., *Proc. Natl. Acad. Sci.*, 74:5463–5467 (1977).

Maxam & Gilbert, A new method for sequencing DNA, *Proc. Natl. Acad. Sci.*, 74:560–64 (1977).

Syvanen et al., "A–Primer Guided Nucleotide Incorporation Assay in the Genotyping of Apolipoprotein E," *Genomics*, 8:684–92 (1990).

Pon, RT, "Solid–phase Supports for Ligonucleotide Synthesis, Methods in Molecular Bilogy vol. 20 Protocols for Oligonucleotides Synthesis," 465–497, Ed. S. Agrawal, Humana Press Inc., Towata, NJ (1993).

Tosquellas et al., The Pro–Oligonucleotide Approach: Solid Phase Synthesis and Preliminary Evaluation of Model Pro–Dodecathymidylates, *Nucleic Acids Res.* 26:9, 2069–74 (1998).

Bologna et al., "The Prooligonucleotide Approach: Synthesis of Mixed Phospodiester and SATE Phosphotreister Prooligonucleotides Using H–Phosphonate and Phosphoramidite Chemistries," *Eur. J. Org. Chem*, 1999, 2353–2358.

"Elimination of Residual Natural Nucleotides from 3'–O–Modified–dNTP Syntheses by Enzymatic Mop–Up," Reprinted from *BioTechniques*, 25:8 814–817 (1998).

Bruno Canard et al., "Catalytic editing properties of DNA plymerases," *Proc. Natl. Acad. Sco.* USA, vol. 92, Nov. 1995.

Marek Kwiatkowski et al., "Synthesis of full–length oligonucleotides: clevage of apurinic molecules on a novel support," *Nucleic Acids Research*; 1996, vol. 24, No. 23.

*Primary Examiner*—Jezia Riley
(74) *Attorney, Agent, or Firm*—Fish & Richardson P.C., P.A.

(57) ABSTRACT

A hydrocarbyldithiomethyl-modified compound of the Formula:

$$R^1-O-CH_2-S-S-R^2$$

or a salt thereof wherein $R^1$ is an organic molecule and $R^2$ is a hydrocarbyl is useful for protecting and/or blocking hydroxyl groups in organic molecules such as nucleotides. The hydrocarbyldithiomethyl-modified compounds can also be used for chemically synthesizing oligonucleotides and for sequencing nucleic acid compounds.

14 Claims, No Drawings

COMPOUNDS FOR PROTECTING HYDROXYLS AND METHODS FOR THEIR USE

FIELD OF THE INVENTION

The invention relates to biological chemistry in general. In particular, the invention relates to protecting hydroxyls in organic molecules.

BACKGROUND OF THE INVENTION

Temporary protection or blocking of chemically reactive functions in biological compounds is an important tool in the field of biological chemistry. To this end, researchers have developed a number of protecting groups. The vast majority of the known protecting groups, however, are acid or base labile and while there are also protecting groups that are labile under neutral conditions, most of these protecting groups are also somewhat acid and base labile. Greene, T W, "Protective Groups in Organic Synthesis", publishers Wiley-Interscience (1981). Furthermore, many protecting groups suffer additional synthesis, side-reaction, and/or solubility problems. For example, only a few protecting groups applied as a part of a linking system between the solid phase and the oligonucleotide can withstand all the rigors of oligonucleotide synthesis and deprotection thereby facilitating the final purification of oligonucleotides free of truncated or depurinated fragments. See "Solid Phase Synthesis," Kwaitkowski et al., PCT International Publication WO 98/08857 (1996). Selective post-synthetic derivatization of oligonucleotides also requires selectively cleavable protecting groups. See, e.g., Kahl & Greenberg, "Introducing Structural Diversity in Oligonucleotides via Photolabile, Convertible C5-substituted Nucleotides," *J Am. Chem. Soc.*, 121(4), 597–604 (1999).

Protecting groups also should be removable. Ideally, the protecting group is removable under mild conditions, for example, without disturbing interactions between biomolecules. These types of protecting groups may be useful for deprotecting oligonucleotides without disturbing interactions between oligo/polynucleotide strands. For example, International Publication WO 96/23807 entitled "Novel Chain Terminators, The Use Thereof for Nucleic Acid Sequencing and Synthesis and a Method of their Preparation" discloses methods that use nucleotides that are reversibly blocked at the 3' hydroxyl group. These reversibly blocked nucleotides can be used in sequencing methods where, unlike the well-known Sanger sequencing method that utilizes terminating dideoxynucleotides, the temporarily 3'-OH-protected intermediates can be converted into nucleotides having a free 3'-OH that may be further extended.

One such sequencing method that uses reversibly blocked nucleotides is known as Sequencing by Synthesis (SBS). SBS determines the DNA sequence by incorporating nucleotides and detecting the sequence one base at a time. To effectively sequence long stretches of a nucleic acid using SBS, it is advantageous to be able to perform multiple iterations of the single nucleotide incorporation Accordingly, SBS-based methods require 3'-OH protecting groups that are removable under conditions that do not distrupt the primer and target DNA interactions. As such, there exists a need for nucleotide triphosphates that are reversibly blocked at the 3' position and which are also effective substrates for DNA polymerases.

SUMMARY OF THE INVENTION

In one aspect, the invention provides a hydrocarbyldithiomethyl-modified compound of the Formula:

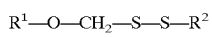

or a salt thereof, wherein $R^1$ is an organic molecule and $R^2$ is a hydrocarbyl. Before undergoing hydrocarbyldithiomethyl-modification, $R^1$ has at least one hydroxyl group, which after modification is in an ether linkage. In one embodiment, $R^2$ further includes a labeling group. The labeling group can be any type of labeling group including fluorescent labeling groups, which can be selected from the group consisting of bodipy, dansyl, fluorescein, rhodamin, Texas red, Cy 2, Cy 4, and Cy 6.

In another embodiment, $R^1$—O represents modified or unmodified amino acids, peptides, proteins, carbohydrates, sterols, ribonucleosides, ribonucleotides, base- and/or sugar-modified ribonucleosides, base- and/or sugar-modified ribonucleotides, deoxyribonucleosides, deoxyribonucleotides, base- and/or sugar-modified deoxyribonucleosides, and base- and/or sugar-modified deoxyribonucleotides. $R^1$ can have more than one hydroxyl group and more than one of the hydroxyl groups can be modified with a hydrocarbyldithiomethyl moiety. For nucleotide embodiments, the hydrocarbyldithiomethyl modification can be at the 2' and/or, 3', and/or 5' hydroxyl positions of the $R^1$—O.

In another embodiment, $R^2$ includes a function that modifies the electron density of the dithio function, thereby modifying the stability of the dithiol. Such a function may be provided by a chemical group containing elements selected from the group consisting of oxygen, nitrogen, sulfur, and silicon.

In another aspect, the invention provides a hydrocarbyldithiomethyl-modified compound of the Formula:

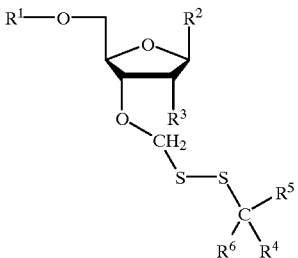

or a salt thereof, wherein $R^1$ is H, a protecting group, phosphate, diphosphate, triphosphate, or residue of a nucleic acid, $R^2$ is a nucleobase, $R^3$ is H, OH, or a protected form of OH; and $R^4$, $R^5$ and $R^6$ are together or separately H, hydrocarbyl, or a residue of a solid support. Suitable hydrocarbyls for $R^4$, $R^5$ and $R^6$ include methyl, ethyl, isopropyl, and t-butyl. In one embodiment, $R^4$, $R^5$ and $R^6$ together or separately further include a labeling group and/or an electron donating function or electron density modifying function. The electron density modifying function can be a heteroatom selected from the group consisting of oxygen, nitrogen, sulfur, and silicon.

In another aspect, the invention provides a compound of the Formula:

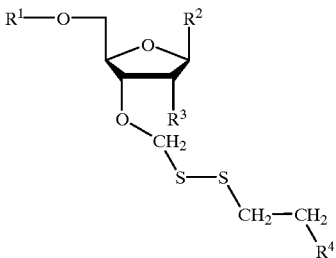

or a salt thereof, wherein $R^1$ is H, a protecting group, a phosphate, diphosphate, or a triphosphate, or a residue of a nucleic acid, $R^2$ is nucleobase, $R^3$ is H or OH, or a protected form of OH, and $R^4$ is H or hydrocarbyl. In one embodiment, $R^4$ is modified with a labeling group. In other embodiments, $R^4$ includes a derivatizable function, or $R^4$ includes nitrogen, or $R^4$ is covalently linked to a solid support.

In another aspect, the invention provides a method for modifying a nucleoside including the steps of: a) contacting a nucleoside having at least one hallogenomethyl-modified hydroxyl group with an thiosulfonate compound thereby forming a thiosulfonated nucleoside; and b) contacting the thiosulfonated nucleoside with a hydrocarbylthiol compound thereby forming a hydrocarbyldithiomethyl-modified nucleoside. Useful thiosulfonate compounds include alkylthiosulfonate and arylthiosulfonate.

In one embodiment, the method includes the step of labeling the hydrocarbyldithiomethyl-modified nucleoside.

In another aspect, the invention provides a method for sequencing a nucleic acid including the steps of: a) contacting a target nucleic acid with a primer wherein at least a portion of the primer is complementary to a portion of the target nucleic acid; b) incorporating a hydrocarbyldithiomethyl-modified nucleotide into the primer; and c) detecting incorporation of the hydrocarbyldithiomethyl-modified nucleotide, wherein the hydrocarbyldithiomethyl-modified nucleotide is complementary to the target nucleic acid at the hydrocarbyldithiomethyl-modified nucleotide's site of incorporation. In one embodiment, the incorporating step is catalyzed by a DNA polymerase. Useful sequencing methods that may use the method disclosed above include minisequencing and sequencing by synthesis whether performed in isolation or performed as a sequencing array.

In another aspect, the invention provides a method for sequencing a nucleic acid including the steps of: a) contacting a target nucleic acid with a primer wherein at least a portion of the primer is complementary to a portion of the target nucleic acid; b) incorporating a first hydrocarbyldithiomethyl-modified nucleotide into the primer; c) detecting the incorporation of the first hydrocarbyldithiomethyl-modified nucleotide; d) removing the hydrocarbyldithiomethyl group from the first incorporated hydrocarbyldithiomethyl-modified nucleotide to form a first elongated primer having a free hydroxyl group; e) incorporating a second hydrocarbyldithiomethyl-modified nucleotide into the first elongated primer; and f) detecting the second hydrocarbyldithiomethyl-modified nucleotide, wherein the first hydrocarbyldithiomethyl-modified nucleotide and the second hydrocarbyldithiomethyl-modified nucleotide are complementary to the target nucleic acid at each nucleotide's site of incorporation. Following the sequencing method steps once will identify the sequence of one nucleobase of the target nucleic acid. Repeating the steps can facilitate identifying the sequence of more than one nucleobase of the target nucleic acid. The conditions of the sequencing method should be such that the primer anneals or hybridizes to the target nucleic acid in a sequence specific manner. In some embodiments the detecting steps are performed before removing the hydrocarbyldithiomethyl group whereas in other embodiments the detecting the incorporation steps are performed after removing the hydrocarbyldithiomethyl group. In some embodiments, the method is optimized for implementing the method in a sequencing array.

In another aspect, the invention provides a compound of the Formula:

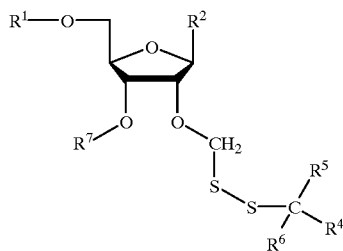

wherein $R^1$ is a H, a protecting group, a phosphate, diphosphate, or a triphosphate, or a residue of a nucleic acid; $R^2$ is a nucleobase; $R^4$, $R^5$ and $R^6$ are together or separately H or hydrocarbyl; and $R^7$ is H, H-phosphonate or phosphoramidite.

In another aspect, the invention provides an oligonucleotide synthesis support of the formula:

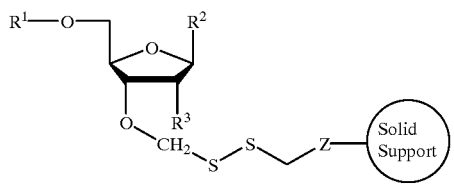

where $R^1$ is H, phosphate, diphosphate, triphosphate, or a protecting group, $R^2$ is a nucleobase, $R^3$ is H, OH, or a protected form of OH, and Z is a group effective for covalent attachment to a solid support, the solid support being effective for securing an oligonucleotide during oligonucleotide synthesis. In some embodiments, Z is selected from the group consisting of amino, amido, ester, and ether.

In another aspect, the invention provides a method for synthesizing an oligonucleotide including the steps of: a) providing a 5' protected first nucleoside secured to a solid support through a linker; b) deprotecting the first nucleoside at its 5' position; c) covalently bonding another 5' protected nucleoside to the first nucleotide at the 5' position of the first nucleoside; d) deprotecting the another nucleoside at it's 5' position; and e) repeating steps c) and d) for incorporating additional protected nucleosides. For this aspect of the invention, the linker secures the first nucleotide to the solid support via a hydrocarbyldithiomethyl bond. This synthesizing method can be optimized for manufacturing oligonucleotide arrays.

In some embodiments, the oligonucleotide synthesis method is effective for inverting the oligonucleotide thereby forming an oligonucleotide having a free 3' hydroxyl and being secured to a solid support via another position.

In another aspect, the invention provides a method for synthesizing an oligoribonucleotide including the steps of: a) providing a first protected ribonucleoside covalently linked to a solid support; b) covalently linking at least one hydrocarbyldithiomethyl-modified ribonucleoside to the first ribonucleoside forming an oligoribonucleotide; c) partially de-protecting the oligoribonucleotide under acidic or basic conditions; and d) contacting the oligoribonucleotide with a reducing agent under neutral conditions thereby completely de-protecting the oligoribonucleotide, wherein the hydrocarbyldithiomethyl-modified ribonucleoside includes a hydrocarbyldithiomethyl group bound at the 2' position of the hydrocarbyldithiomethyl-modified ribonucleoside. Such a method is effective for preventing cleavage or migration of internucleotide phosphate bonds during deprotection and is also effective for inverting the oligoribonucleotide thereby forming a solid phase bound oligonucleotide having a free 3' hydroxyl. In some embodiments, the pH is neutral and can be about 7 or range from about 5 to about 9. In other embodiments, the first protected ribonucleoside is secured or covalently linked to the solid support via a hydrocarbyldithiomethyl bond.

In another aspect, the invention provides a method for sequencing a nucleic acid including the steps of: a) providing a primer array including a plurality of sequencing primers; b) contacting a target nucleic acid with the primer array thereby forming target-primer complexes between complementary portions of the sequencing primers and the target nucleic acid; c) incorporating a first hydrocarbyldithiomethyl-modified nucleotide into at least one sequencing primer portion of the target-primer complexes, the first hydrocarbyldithiomethyl-modified nucleotide being complementary to the target nucleic acid; and d) detecting the incorporation of the first hydrocarbyldithiomethyl-modified nucleotide, wherein the first hydrocarbyldithiomethyl-modified nucleotide is complementary to the target sequence at the first hydrocarbyldithiomethyl-modified nucleotide's site of incorporation. In one embodiment, the method further includes the steps of: e) removing the hydrocarbyldithiomethyl group from the first incorporated hydrocarbyldithiomethyl-modified nucleotide to form a first elongated target-primer complex having a free 3' hydroxyl group; f) incorporating a second hydrocarbyldithiomethyl-modified nucleotide into the first elongated target-primer complex; and g) detecting the second hydrocarbyldithiomethyl-modified nucleotide, wherein the second hydrocarbyldithiomethyl-modified nucleotide is complementary to the target sequence at the second hydrocarbyldithiomethyl-modified nucleotide's site of incorporation. As with other methods described herein, the detecting step can be performed before or after removing a hydrocarbyldithiomethyl moiety. This sequencing method is effective for producing a plurality of nucleotide sequences wherein the nucleotide sequences correspond to overlapping nucleotide sequences of the target nucleic acid.

In another aspect, the invention provides a method for sequencing a nucleic acid including the steps of: a) providing a target nucleic acid array including a plurality of target nucleic acids; b) contacting a sequencing primer with the target nucleic acids thereby forming target-primer complexes between complementary portions of the sequencing primers and the target nucleic acids; c) incorporating a first hydrocarbyldithiomethyl-modified nucleotide into at least one sequencing primer portion of the target-primer complexes, the first hydrocarbyldithiomethyl-modified nucleotide being complementary to the target nucleic acid; and d) detecting the incorporation of the first hydrocarbyldithiomethyl-modified nucleotide, wherein the first hydrocarbyldithiomethyl-modified nucleotide is complementary to the target sequence at the first hydrocarbyldithiomethyl-modified nucleotide's site of incorporation. As with other methods described herein, the detecting step can be performed before or after removing a hydrocarbyldithiomethyl moiety. This sequencing method is effective for producing a plurality of nucleotide sequences wherein the nucleotide sequences correspond to overlapping nucleotide sequences of the target nucleic acid.

In another aspect, the invention provides a method for synthesizing an oligonucleotide that includes the steps of: a) providing a 5' protected first nucleoside covalently bonded to a solid support through a hydrocarbyldithiomethyl containing linker; b) deprotecting the first nucleoside at its 5' position; c) covalently bonding another 5' protected nucleoside to the first nucleotide at the 5' position of the first nucleoside; d) deprotecting the another nucleoside at its 5' position; e) optionally repeating steps c) and d) for adding additional protected nucleosides thereby producing an oligonucleotide; f) optionally selectively cleaving a protecting group from the oligonucleotide thereby forming a partially deprotected oligonucleotide; g) selectively cleaving the hydrocarbyldithiomethyl containing linker; and h) isolating the partially deprotected oligonucleotide. In one embodiment, the method further includes the step of modifying the 3' terminus with a reactive or detectable moiety. In another embodiment, at least one of the 5' protected nucleosides contains a hydrocarbyldithiomethyl moiety.

Advantages of the invention include introducing temporary or reversible mutations in proteins, facilitating continuous sequencing methods, blocking reactive species during chemical syntheses, masking chemical groups for manufacturing purposes, using hydroxyl groups to introduce labeling groups into organic molecules, and other similar uses. It is to be understood that particular embodiments of the invention described herein may be interchanged with other embodiments of the invention.

Unless otherwise defined, all technical and scientific terms used herein have the same meaning as commonly understood by one of ordinary skill in the art to which this invention belongs. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION

The present invention relates to hydrocarbyldithiomethyl-modified compounds having modified and/or protected hydroxyl groups, methods for manufacturing such compounds, and methods for their use. The general formula for the hydroxyl-modifying moiety contains a dithiol. The dithiol is designed so that modified hydroxyls can be de-protected under neutral conditions using mild reducing agents.

A hydrocarbyldithiomethyl-modified compound is shown in Formula 1:

  (Formula 1)

wherein $R^1$ represents any organic molecule that had at least one free hydroxyl group before undergoing the hydrocarbyldithiomethyl modification. In Formula 1, "O" is the oxygen atom of the hydroxyl group, which is now protected in an ether linkage. For example, before modification, $R^1$ can be a modified or unmodified amino acid or analog thereof, oligonucleotide, peptide, protein, carbohydrate, deoxyribonucleoside, deoxyribonucleotide, ribonucleoside, ribonucleotide, base- and/or sugar-modified ribonucleoside, base- and/or sugar-modified deoxyribonucleoside, base- and/or sugar-modified nucleotide, sterol or steroid, as long as the organic molecule selected has at least one hydroxyl group capable of being hydrocarbyldithiomethyl modified.

As referred to herein, oligonucleotides refers to any nucleotide polymer including polymers of deoxyribonucleotides, ribonucleotides, nucleotide analogs and mixtures thereof.

When $R^1$—O is an organic molecule having more than one free hydroxyl group, any number of the free hydroxyls may be modified with a hydrocarbyldithiomethyl moiety. Alternatively, one or more of the additional hydroxyl groups can be modified and/or protected with other known hydroxyl modifying compounds or left unmodified. Different protecting groups may be used to protect different hydroxyl groups. Useful protecting groups, other than the hydrocarbyldithiomethyl-based groups described herein, and methods for their use are known to those of skill in the art and include fluorenylmethyloxycarbonyl (FMOC), 4-(anisyl)diphenylmethyltrityl (MMTr), dimethoxytrityl (DMTr), monomethoxytrityl, trityl (Tr), benzoyl (Bz), isobutyryl (ib), pixyl (pi), ter-butyl-dimethylsilyl (TBMS), and 1-(2-fluorophenyl)-4-methoxypiperidin 4-yl (FPMP). See, e.g., Greene, T W, "Protective Groups in Organic Synthesis", publishers Wiley-Interscience (1981); Beaucage & Iyer, "Advances in the Synthesis of Oligonucleotides by the Phosphoramidite Approach," *Tetrahedron,* 48(12):2223–2311 (1992); Beaucage & Iyer, "The Synthesis of Specific Ribonucleotides and Unrelated Phosphorylated Biomolecules by the Phosphoramidite Method," *Tetrahedron,* 49(46):10441–10488 (1993); and Scaringe et al., "Novel RNA Synthesis Method Using 5'-O-silyl-2'-O-orthoester Protecting Groups," *J. Am. Chem. Soc.,* 120:11820–21 (1998). The choice of protective group can be dictated by the type of organic molecule to be protected and the methods employed. Therefore, different organic molecules such as peptides, oligonucleotides, carbohydrates, and steroids may each use different protective groups. A hydroxyl with a known protecting group or a hydrocarbyldithiomethyl moiety attached to it can be referred to as a protected form of the hydroxyl.

In Formula 1, $R^2$ represents a hydrocarbyl group. As used herein, hydrocarbyl groups include any organic radical having a carbon atom directly attached to the remainder of the molecule, e.g., saturated and unsaturated hydrocarbons, straight- and branched-chain aliphatic hydrocarbons, cyclic hydrocarbons, aromatic hydrocarbons, heterocyclic hydrocarbons, heteroaromatic hydrocarbons, and substituted hydrocarbons such as hydrocarbons containing heteroatoms and/or other functional modifying groups. The hydrocarbyl group may be covalently linked to a solid support (described below), labeling group or another organic molecule.

Suitable hydrocarbons include alkyls (e.g., methyl, ethyl, propyl, butyl, pentyl, hexyl, heptyl, octyl, nonyl, decyl, undecyl, dodecyl, tridecyl, and heptadecyl); alkoxy; alkenyl; $C_{3-8}$ alkenyloxy; alkynyl; alkynyloxy; $C_{3-20}$ cycloalkyl (e.g. cyclopropyl, cyclobutyl or cyclopentyl) in which the cycloalkyl may be substituted by one or more hydrocarbyls or heteroatoms; $C_{3-8}$ cycloalkoxy (e.g. cyclopentoxy); $C_{4-8}$ cycloalkenyloxy (e.g. cyclopenten-3-yloxy); aryl (e.g. phenyl) or aralkyl (e.g. benzyl) in which the aryl may be substituted with one or more $C_{1-4}$ alkyl, halogen, hydroxy, $C_{1-4}$ alkoxy, amino or nitro; aryloxy (e.g. phenoxy); aralkoxy (e.g. benzyloxy) in which the aryl may be substituted with one or more $C_{1-4}$ alkyl, halogen, hydroxy, $C_{1-4}$ alkoxy, amino or nitro; $C_{1-6}$ hydroxyalkyl (e.g. hydroxyethyl); and $C_{1-6}$ alkoxyalkyl (e.g. Methoxysilyl). In addition, all iso, sec and tert isomers of the aliphatic hydrocarbons are included such as isopropyl and t-butyl.

Substituted hydrocarbon groups are hydrocarbons containing non-hydrocarbon substituents. Suitable substituents include oxygen, nitrogen, sulfur, phosphorous, halogens (e.g., bromine, chlorine, iodine, and fluorine), hydroxy, carbalkoxy (especially lower carbalkoxy) and alkoxy (especially lower alkoxy), the term, "lower" denoting groups containing 7 or less carbon atoms.

Other functional modifying groups capable of moderating the reactivity or lability of the disulfide bond or facilitate synthesizing compounds of Formula 1 can be incorporated into $R^2$. Useful functional modifying groups are known and include heteroatoms such as oxygen, nitrogen, sulfur, phosphorous, and halogens. Functional modifying groups also include heterogroups such as amino, nitro, and cyano. These groups may function as an electron withdrawing or donating groups. Skilled artisans know whether electron withdrawing or donating groups would be appropriate.

$R^2$ may further include a labeling group. Useful labeling groups are known to those of ordinary skill in the art and include radioactively labeled groups, luminescent groups, electroluminescent groups, fluorescent groups, and groups that absorb visible or infrared light. Examples of useful fluorescent labels include bodipy, dansyl, fluorescein, rhodamin, Texas red, Cy 2, Cy 4, and Cy 6. Additional useful labels can be found in the "Handbook of Fluorescent probes and Research Chemicals," by Richard P. Haugland and "Nonisotopic DNA Probe Techniques," Ed. Larry J. Kricka (Academic Press, Inc. 1992).

Hydrocarbyldithiomethyl-modified compounds can be created from available compounds using the following illustrative method. A free hydroxyl on a hydroxyl-containing molecule is modified to form a methylthiomethyl ether. The methylthiomethyl ether can be formed by reacting the hydroxyl with a mixture of acetic anhydride, acetic acid and dimethyl sulfoxide (DMSO). See Hovinen et al., "Synthesis of 3'-O-(ω-Aminoalkoxymethyl)thymidine 5'-Triphosphates, Terminators of DNA synthesis that Enable 3'-Labeling," *J Chem. Soc. Perkin Trans.* 1, pp. 211–217 (1994). It is to be understood that, if the molecule to be modified contains more than one hydroxyl group, it may be necessary to first protect or block one or more hydroxyl groups that are not to be hydrocarbyldithiomethyl-modified.

The methylthiomethyl ether-derivatized compound is then converted to a more reactive species such as a halogenatedmethyl ether. Useful halogens include bromine, chlorine, and iodine. The halogenation step can be carried out using any method including treating the methylthiomethyl ether with N-bromosuccinimide (NBS), or $Br_2$ in dry chlorethane, or $SOCl_2$, or N-iodosuccinimide (NIS).

The halogenated methyl ether compound is then converted to a hydrocarbylthiolsulfonate reagent by treating it with an alkyl hydrocarbylthiolsulfonate. See Bruice & Kenyon, "Novel Alkyl Alkanethiolsulfonate Sulfhydryl reagents, Modification of Derivatives of L-Cysteine," *J Protein Chem.,* 1(1):47–58 (1982) and Plettner et al., "A Combinatorial Approach to Chemical Modification of Subtilisin *Bacillus lentus,*" *Bioorganic & Medicinal Chem. Lett.* 8, pp. 2291–96 (1998).

Contacting the hydrocarbylthiolsulfonate reagent with any unsubstituted or substituted thiol can cause displacement of the sulfonyl moiety thereby creating a hydrocarbyldithiomethyl-modified compound. Useful thiols include branched- and straight-chain aliphatic thiols, aromatic thiols, heteroaromatic thiols, substituted aliphatic thiols, functionally modified thiols, and fluorophore labeled thiols. Functionally modified thiols include thiols substituted at a carbon atom with an atom or group capable of altering the reactivity of a dithio moiety, capable of facilitating subsequent labeling, or capable of facilitating immobilization of the modified compound. Useful examples of modifying groups include amino, amido, hydroxyl, silyl, cyano, carboxylic esters, or other carboxylic substitutions.

It may be particularly useful to use the compounds of Formula 1 when $R^1$ contains nucleobase. As used herein, nucleobase includes any natural nucleobase, synthetic nucleobase, and/or analog thereof. Natural nucleobases include adenine, guanine, cytosine, thymine, uracil, xanthine, hypoxanthine, and 2-aminopurine. Synthetic nucleobases are typically chemically synthesized and are analogues of the natural nucleobases. Synthetic nucleobases are capable of interacting or hydrogen bonding with other nucleobases. Nucleobase containing compounds can include both nucleosides and nucleotides. Nucleosides and nucleotides can be modified at the 5', 3' and/or 2' hydroxyl positions. Known methods for protecting the 5', 3' and/or 2' positions may be used in conjunction with the methods described herein to modify individual hydroxyl positions.

For example, the compound shown in Formula 2

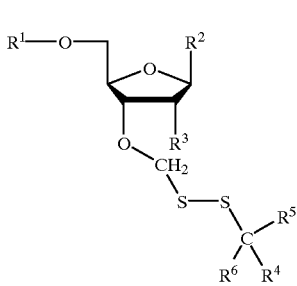

(Formula 2)

or a salt thereof can be synthesized using the methods described herein. In Formula 2, $R^1$ is H, a protecting group, phosphate, diphosphate, triphosphate, or a residue of a nucleic acid; $R^2$ is a nucleobase; $R^3$ is H, OH, or a protected form of OH; $R^4$, $R^5$ and $R^6$ are together or separately H, hydrocarbyl, or a residue of a solid support. For example, $R^4$, $R^5$ and $R^6$ include together or separately H, methyl, ethyl, isopropyl, t-butyl, phenyl, or benzyl. It may be useful to include a substituted hydrocarbon having an electron density modifying group containing a heteroatom or other functional modifying group at positions $R^4$, $R^5$ or $R^6$. For example, $R^4$, $R^5$ or $R^6$ could be methyleneamine, ethyleneamine, or contain an amino group. As an optional aspect, $R^4$, $R5$ or $R^6$ can be modified with a labeling group.

Another illustrative example of useful hydrocarbyldithiomethyl-modified compounds include the compounds of Formula 3

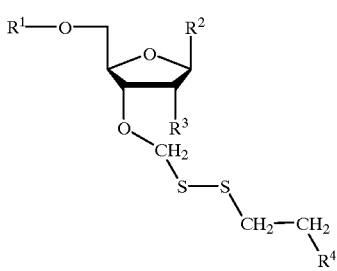

(Formula 3)

or a salt thereof, wherein $R^1$ is H, a protecting group, a phosphate group, diphosphate group, or a triphosphate group; $R^2$ is nucleobase; $R^3$ is H or OH, or a protected form of OH; and $R^4$ is H, a heteroatom, a heterogroup, hydrocarbyl or a label-modified hydrocarbyl. $R^4$ may be used to link the compound of Formula 3 to a solid support.

A nucleobase containing hydrocarbyldithiomethyl-modified compound can be chemically synthesized using the methods described herein. For example:

Compound A (wherein $R^1$ is a suitable protecting group, $R^2$ is a nucleobase, and $R^3$ is either a protected hydroxyl or H) is treated with a mixture of DMSO, acetic acid, and acetic anhydride to form a methylthiomethyl ether (compound B)

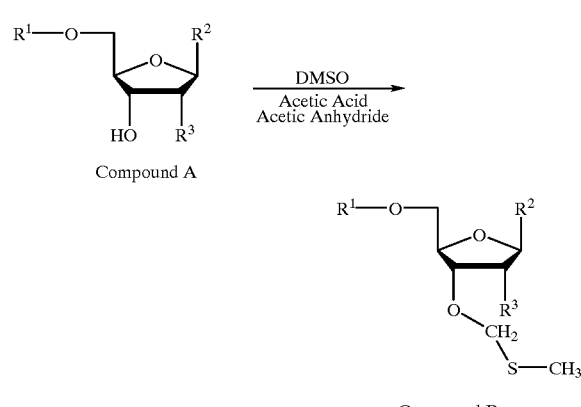

The methylthiomethyl ether (compound B) is converted to a more reactive halogenated species (compound C) wherein X is Br, Cl, or I.

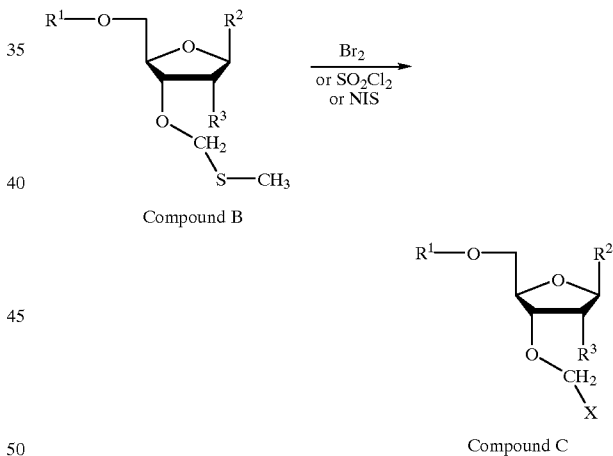

Compound C is treated with an alkyl- or arylthiosulfonate such as methylphenylthiosulfonate (MePhSO$_2$SH) to prepare compound D.

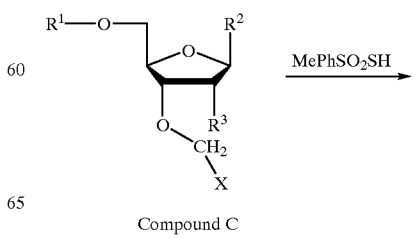

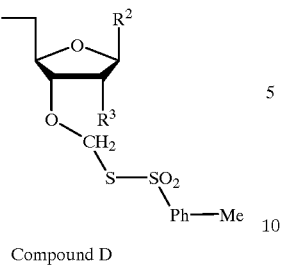

Compound D

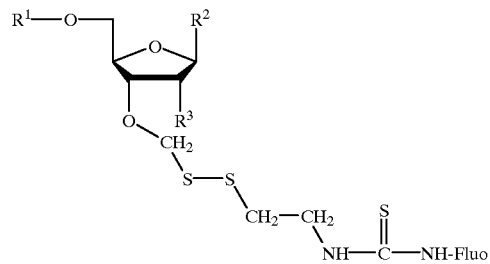

Compound F

Compound D is treated with a hydrocarbyldithiol compound such as 2-thioaminoethane to form a hydrocarbyldithiomethyl-modified nucleobase (compound E). In some instances, compound E may be the final product.

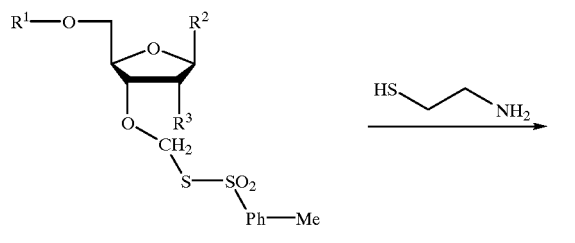

Compound D

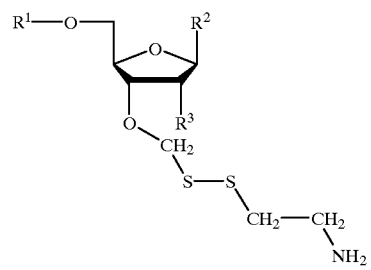

Compound E

When the thiol used to form compound E contains a modifiable substituent, compound E can be further modified or labeled as shown below. Compound E can be treated under known conditions with an isothiocyanate form of a suitable fluorophore (such as fluoresceinisothiocyanate) to form compound F. Compound F can be further modified. For example, $R^1$ can be replaced with a mono, di, or triphosphate group. Forming a triphosphate can facilitate using the nucleobase containing compounds in enzymatic and template-dependent DNA or RNA synthesis reactions.

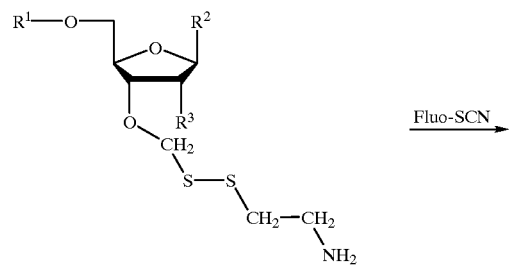

Compound E

Hydrocarbyldithiomethyl-modified nucleotide triphosphates protected at the 3' position (as described above) are useful for any sequencing method. 3'-hydrocarbyldithiomethyl-modified nucleotide triphosphates can terminate extension of the primer sequence when used in a DNA polymerase-mediated sequencing method. Unlike most conventional dideoxy methods where incorporation of the dideoxynucleotide is permanent, however, termination using a hydrocarbyldithiomethyl-modified nucleotide is reversible. Thus, one of the benefits associated with using a hydrocarbyldithiomethyl-modified nucleotides for sequencing is that the sequencing reaction can be stopped and started by utilizing the labile nature of the protecting group. That is, the hydrocarbyldithiomethyl-moiety can be removed by reducing the disulfide bond of the protecting group. Reducing the disulfide creates an unstable intermediate that spontaneously decomposes to produce a free 3' hydroxyl, which can be used for attaching another nucleotide. The disulfide of the hydrocarbyldithiomethyl-moiety can be reduced using any reducing agent. Suitable reducing agents include dithiothreitol (DTT), mercaptoethanol, dithionite, reduced glutathione, reduced glutaredoxin, reduced thioredoxin, and any other peptide or organic based reducing agent, or other reagents known to those of ordinary skill in the art. Reduction can be achieved under neutral conditions. It is to be understood that the reduction step leading to the spontaneous decomposition of the intermediate is applicable to all hydrocarbyldithiomethyl-modified compounds. Accordingly, it may be necessary to adjust the conditions of conventional sequencing reactions using DNA polymerase enzymes that utilize reduced thioredoxin so that free thiols are not present when the hydrocarbyldithiomethyl-modified nucleotides are added.

The compounds of Formulas 1–3 are useful as reagents in almost any method for sequencing a nucleic acid molecule. General methods for sequencing nucleic acids are known and include dideoxy sequencing methods (Sanger et al., Proc. Natl. Acad. Sci., 74:5463–5467 (1977), chemical degradation methods (Maxam & Gilbert, Proc. Natl. Acad. Sci., 74:560–64 (1977), minisequencing methods (Syvänen et al., i Genomics, 8:684–92 (1990), and sequencing by synthesis (i.e., multiple iterations of the minisequencing method). It is common practice in these methods to block the 3' hydroxyl of some of the nucleotides. Further, the sequencing by synthesis method requires the availability of nucleotides having a reversibly blocked 3' hydroxyl.

For example, a sequencing method can proceed by contacting a target nucleic acid with a primer. The target nucleic acid can be any nucleic acid molecule. The primer would also be a nucleic acid molecule. Typically, the primer is shorter than the nucleic acid to be sequenced. Methods for preparing nucleic acids for sequencing and for manufacturing and preparing primer sequences to be used in a sequencing reaction are known. It is advantageous to design the primer so that at least a portion of the primer is complementary to a portion of the target nucleic acid. It is also advantageous to design the primer so that the whole primer is complementary to a portion of the target nucleic acid.

During a sequencing reaction, the primer and target nucleic acid sequences are combined so that the primer anneals or hybridizes to the target nucleic acid in a sequence specific manner. A DNA polymerase enzyme is then used to incorporate additional nucleotides into the primer in a sequence specific or template-dependent manner such that the nucleotide incorporated into the primer is complementary to the target nucleic acid. For example, a 3'-hydrocarbyldithiomethyl-modified nucleotide or a mixture of nucleotides is added to the sequencing reaction at a sufficient concentration so that the DNA polymerase incorporates into the primer a single hydrocarbyldithiomethyl-modified nucleotide that is complementary to the target sequence. The incorporation of the hydrocarbyldithiomethyl-modified nucleotide can be detected by any known method that is appropriate for the type of label used.

A second or subsequent round of incorporation for the hydrocarbyldithiomethyl-modified nucleotide can occur after incubating the primer target sequence complex with a suitable reducing agent. Further, each round of incorporation can be completed without disrupting the hybridization between primer and target sequence. After reduction of the disulfide, the 3'-OH becomes unblocked and ready to accept another round of nucleotide incorporation. The incorporation and reduction steps can be repeated as needed to complete the sequencing of the target sequence. In this way, it may be advantageous to differentially label the individual nucleotides so that incorporation of different nucleotides can be detected. Such a method can be used in single sequencing reactions, automated sequencing reactions, and array based sequencing reactions.

Hydrocarbyldithiomethyl-modified deoxyribonucleotides and ribonucleotides can also be used for synthesizing oligonucleotides. Chemical synthesis of oligoribonucleotides has an added complexity compared to oligodeoxyribonucleotides due to the presence of the 2'-OH in ribonucleosides. The 2'-OH must be protected during synthesis. Further, the blocking group must be removable during final deblocking. Conditions used for deblocking conventional protecting groups can promote cleavage and/or migration of internucleotide linkages, i.e., the 5'-3' linkage of the oligonucleotide may migrate to form a 5'-2' linkage. This cleavage is both acid and base catalyzed, while migration is acid catalyzed. As such, blocking the 2'-OH with a hydrocarbyldithiomethyl moiety is advantageous because the bond is: 1) stable under conventional/standard acidic and basic conditions while other blocked regions of the oligoribonucleotide are deprotected, and 2) the hydrocarbyldithiomethyl moiety can be removed under neutral conditions using a simple reducing agent.

A method for synthesizing an oligoribonucleotide using ribonucleosides modified at the 2'-OH position with a hydrocarbyldithiomethyl moiety can proceed as follows. A first nucleoside is linked to a solid support using known methods. See, e.g., Pon, RT, "Chapter 19 Solid-phase Supports for Oligonucleotide Synthesis," *Methods in Molecular Biology Vol. 20 Protocols for Oligonucleotides and Analogs*, 465–497, Ed. S. Agrawal, Humana Press Inc., Towata, N.J. (1993). The 2'-OH modifying moiety can be a hydrocarbyldithiomethyl moiety or any other known protecting group (e.g., ester). Alternatively, the first ribonucleoside monomer is linked to a solid support using known methods but also having a linker as shown in Formula 6 (described below). It is to be understood that the 5'-OH and the 3'-OH are also protected as needed using known methods or the methods described herein. After the initial nucleoside is tethered to the solid support, additional hydrocarbyldithiomethyl-modified ribonucleoside monomers are added to the growing oligoribonucleotide using any of the existing strategies for internucleotide bond formation. The completed oligoribonucleotide is then deblocked at all positions except the 2'-O-position by using ammonia. The partially deblocked oligoribonucleotide is then contacted with a reducing agent under neutral conditions to achieve the final deprotection. Neutral conditions are conditions that do not promote migration of internucleotide linkages. Conditions having a pH value ranging from about 5 to about 9 and any particular value therebetween, e.g., 7, are considered neutral.

A suitable ribonucleoside for use in a chemical oligonucleotide synthesis reaction utilizing a hydrocarbyldithiomethyl-modified ribonucleoside monomer is shown at Formula 4

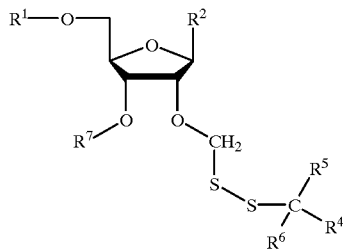

(Formula 4)

wherein $R^1$ is a H or a protecting group, $R^2$ is a nucleobase, R4, $R^5$ and $R^6$ are together or separately H or hydrocarbyl. $R^7$ may be H, H-phosphonate or phosphoramidite.

An example of Formula 4 is shown at Formula 5

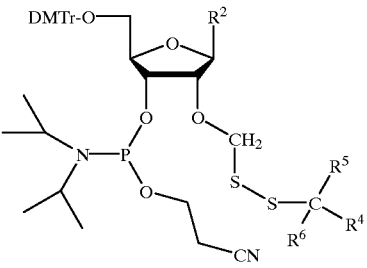

(Formula 5)

wherein $R^2$ is a nucleobase, $R^4$, $R^5$ and $R^6$ are together or separately H or hydrocarbyl. Alternatively, other known blocking groups may be used to block the nucleoside at the 5'-OH and 3'-OH positions according the needs of the skilled artisan.

Suitable ribonucleosides (as described above) can be prepared using known methods and/or the methods described herein for adding a hydrocarbyldithiomethyl moiety to a nucleoside.

Chemical synthesis methods using the oligodeoxyribonucleotides and oligoribonucleotides described herein can include methods for inverting the orientation of the oligonucleotides on the solid support. International Application WO 98/51698 entitled "Synthesis of Oligonucleotides" discloses methods for preparing immobilized oligonucleotides and for their subsequent inversion to produce oligonucleotides having a free 3'-OH. These methods together with the compounds and methods described herein can be used together to produce oligonucleotide arrays. The arrays are useful for binding and sequencing reactions, especially automated sequencing reactions.

Chemical synthesis methods using the oligodeoxyribonucleotides and oligoribonucleotides described herein can include methods for preparing oligonucleotides having different hydrophobic characteristics. Oligonucleotides can be designed to be more or less hydrophobic by using selectively cleavable protecting groups. To alter the hydrophobic character of the nucleotide, a subset of protecting groups is removed after synthesizing the oligonucleotide. By altering the ratio of protecting groups attached the finished oligonucleotide to the number of protecting groups removed, the hydrophobicity of the finished oligonucleotide can be controlled. These types of oligonucleotides can be useful as pro-oligonucleotides for antisense drug treatment methods for a variety of disease states. The article Tosquellas et al., "The Pro-Oligonucleotide Approach: Solid Phase Synthesis And Preliminary Evaluation Of Model Pro-Dodecathymidylates," *Nucleic Acids Res.* 26:9, 2069–74 (1998) provides an example of such pro-oligonucleotides.

Oligonucleotides having altered hydrophobicities can be synthesized by following the methods described herein. For example, a first protected nucleoside is covalently attached to a solid support. Additional protected nucleosides are added according to methods described herein to assemble an oligonucleotide. The additional nucleosides may each have different protecting groups. A subset of the protecting groups can be removed. After reducing the dithiobond, the oligonucleotide is removed from the solid phase, washed out and collected. This method allows for isolation of an almost completely protected oligonucleotide. The 3'-terminus of the oligonucleotide can be modified with a reactive or detectable moiety. The oligonucleotide fragments activated at the 3'-position can be used for constructing larger oligonucleotides or synthetic genes. They may also be used in a method for combinatorial synthesis of gene variants lacking any unwanted stop codons.

Hydrocarbyldithiomethyl-modified compounds may also be used to link molecules to a solid support. In particular, it may be advantageous to use hydrocarbyldithiomethyl-modified compounds for chemical synthesis of organic molecules such as oligonucleotides, peptides, and carbohydrates. Several methods for coupling organic molecules to solid supports are known. See, e.g., Pon, RT, "Chapter 19 Solid-phase Supports for Oligonucleotide Synthesis," *Methods in Molecular Biology Vol. 20 Protocols for Oligonucleotides and Analogs*, 465–497, Ed. S. Agrawal, Humana Press Inc., Towata, N.J. (1993). Only a few methods, however, provide linkages that are inert under acidic and basic conditions, and yield a free hydroxyl group after cleaving the linkage. For example, photochemically labile o-nitrobenzyl ether linkages, siloxyl linkages, and disiloxyl type linkages that are cleavable using fluoride anions, are both inert under acidic and basic conditions and yield a free hydroxyl group after cleaving the linkage. Use of the above linkages is sometimes impractical or associated with unwanted side reactions. The hydrocarbyldithiomethyl-modified linkages described herein are cleavable under neutral conditions.

Accordingly, an oligonucleotide synthesis support can include the molecule shown in Formula 6

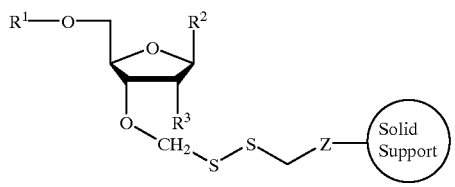

(Formula 6)

wherein $R^1$ is H, phosphate, diphosphate, triphosphate, or a 5'-protecting group, $R^2$ is a nucleobase, $R^3$ is H, OH, or a protected form of OH, and Z is a group effective for covalent attachment to a solid support. Examples of Z include amido, ether and any other linking function groups known to those of ordinary skill in the art. Such a linker capable of being coupled to a solid support can be effective for securing an oligonucleotide during oligonucleotide synthesis.

An example of a linker described in Formula 6 is shown in Formula 7

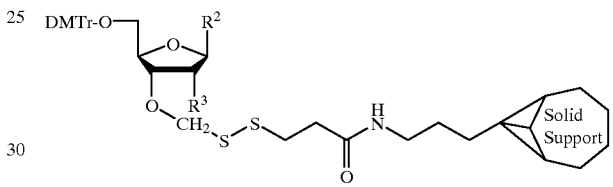

Formula 7 wherein $R^2$ is a nucleobase, $R^3$ is H, OH, or a protected form of OH.

Chemical synthesis of an oligonucleotide can be done by attaching a first nucleoside monomer to a solid support. Any known solid support can be used including non-porous and porous solid supports and organic and inorganic solid supports. Useful solid supports include polystyrenes, cross-linked polystyrenes, polypropylene, polyethylene, teflon, polysaccharides, cross-linked polysaccharides, silica, and various glasses. In some instances, certain solid supports are not fully compatible with aspects of oligonucleotide synthesis chemistry. For example, strong alkaline conditions at elevated temperatures used for deprotection of synthetic oligonucleotides or fluoride anions such as those provided by tetrabutylammonium fluoride cannot be applied to silica or glass supports. Conventional linkers and methods for attaching monomers or oligonucleotides to a solid support are known. See Beaucage & Iyer, *Tetrahedron*, 48(12): 2223–2311 (1992).

The invention will be further described in the following examples, which do not limit the invention as set forth in the claims.

EXAMPLE 1

Synthesizing 5'-O-FMOC-thymidine

Thymidine (10 mmol) was dried by coevaporation with dry pyridine (2×30 ml), re-dissolved in dry pyridine (50 ml) and cooled using an acetone/carbon dioxide bath to a temperature of −20° C. The thymidine solution was magnetically stirred and a dichloromethane solution of FMOC-Cl (12 mmol, 1.2 eq. in 20 ml DCM) was added over a period of 60 minutes. The reaction mixture was warmed to room temperature and stirred for additional 60 minutes. The reaction mixture was partitioned between saturated sodium hydrogen carbonate (250 ml) and dichloromethane (3×100 ml). The organic phase was saved, combined, evaporated and dried by coevaporation with toluene (2×50 ml) forming an oily residue. A pure product was crystallized from the oily residue using dichloromethane (30 ml) and benzene (50 ml) as solvent. Yield 76%—white crystals.

EXAMPLE 2

Synthesizing 5'-O-FMOC-3'-O-methylthiomethyl-thymidine

The produce of Example 1 (5'-O-FMOC-Thymidine (7.0 mmol)) was dissolved in 50 ml of an acetic acid:acetic anhydride:DMSO solution (11:35:54, v/v) at 20° C. according to (Zavgorodny et al. (1991) *Tetrahedron Lett.* 32:7593–7596). The solution was stirred at 20° C. for 4 days resulting in a complete conversion of the starting material to methylthiomethyl ether derivative as monitored by thin layer chromatography (TLC). The solvent was evaporated using a rotary evaporator at 50° C. under high vacuum (oil pump). The residue was dissolved in ethanol (30 ml) and poured into vigorously stirred water (500 ml). A solid material precipitated and was filtered off. The precipitate was then dissolved in dichloromethane, coevaporated with toluene (2×50 ml), and flash chromatographed using dichloromethane:chloroform (1:1 v:v) as the solvent to give the final product as an oil. Yield 72%.

EXAMPLE 3

Synthesizing 5'-O-FMOC-3'-O-(4-methylphenylthiosulfonatemethyl)thymidine

The product of Example 2 (5'O-FMOC-3'-O-methylthiomethyl-thymidine (4.0 mmol)) was dissolved in a solution of dichloromethane (20 ml) and bromine ($Br_2$) (226 µl) was added at 20° C. After a 10 minute incubation, a potassium salt of p-toluenethiosulfonic acid (10.0 mmol) dissolved in dry DMF (10 ml) and lutidine (1.5 ml) was added. The reaction mixture was stirred for an additional 120 minutes, quenched by addition of saturated $NaHCO_3$ and extracted with dichloromethane (3×50 ml). The resulting organic phase was evaporated, coevaporated with toluene, and flash chromatographed using chloroform as the final solvent. The final product was isolated as an oil. Yield 58%.

EXAMPLE 4

Synthesizing 3'-O-hydrocarbyldithiomethyl) thymidine derivatives

The product of Example 3 (1 mmol) is dissolved in pyridine (5.0 ml) and an appropriate thiol, such as reduced cystamine ("R"SH, i.e., hydrocarbylthiol) (1.1 mmol) dissolved in pyridine (2.0 ml), is added.

The mixture is stirred for 60 min at 20° C., then extracted using conventional bicarbonate extraction methods and purified by flash chromatography. In some instances it may be advantageous to continue the synthetic process by addition of dry triethylamine (4.0 mmol) in order to remove the 5'-O-FMOC protecting group. After 45 minutes the solvent is evaporated and the 5'-OH derivative is isolated by chromatography after the standard work-up using aqueous $NaHCO_2$ and dichloromethane and evaporating the organic extracts.

EXAMPLE 5

Synthesizing 3'-O-(2-N-dansylethyldithiomethyl)-thymidine

The general procedure of Example 4 is followed using N-dansylethanethiol as the thiol. N-dansylethanethiol is prepared by reacting cystamine dihydrochloride with dansyl chloride followed by reducing the disulfide with sodium borohydride. N-dansylethanethiol is isolated using rapid silica gel purification.

After forming the desired 2-N-dansylethyldithiomethyl linkage, the 5' FMOC group is removed using known methods.

EXAMPLE 6

Synthesizing 3'-O-(2-N-dansylethyldithiomethyl)-thymidine-5'-triphosphate tetralithium salt The product of Example 5 (3'-O-(2-N-dansylethyldithiomethyl)-thymidine (0.1 mmol)) is dried by coevaporation with dry pyridine (2×5 ml) and dissolved in dry acetonitrile (2.0 ml). Phosphorotristriazolide (0.1 M) in dry acetonitrile is prepared from phosphorus oxychloride and triazole as described in Kraszewski & Stawinski, *Tetrahedron Lett.*, 21:2935–2936 (1980). Phosphorotristriazolide (1.5 ml, 1.5 eq.) is added to the 3'-O-(2-N-dansylethyldithiomethyl)-thymidine at room temperature or 20° C. The mixture is stirred for 5 minutes at which point n-butylammonium pyrophosphate in dry DMF (0.2 M, 1.5 ml, 2.0 eq.) is added. The mixture is stirred overnight at 20° C. Water (2 ml) is then added and hydrolysis of the phosphates occurs (180 min). The nucleotide triphosphate is applied to an anion exchange column Mono Q ™ (Pharmacia Biotech. Sweden) equilibrated with triethylammonium bicarbonate (TEAB) (0.01 M) and eluted from the Mono Q ™ column using a linear gradient of TEAB (0.85M):acetonitrile (33%, v/v). The isolated 3'-O-(2-N-dansylethyldithiomethyl)thymidine-5'-triphosphate tetralithium salt fraction is evaporated, coevaporated with water and passed through a Dowex 50W×8 (BDH) in a lithium form to accomplish exchange of the triethylammonium to the lithium ions. At this point the hydrocarbyldithiomethyl-modified nucleotide is ready to be used.

Other aspects, advantages, and modifications are within the scope of the following claims.

What is claimed is:

1. A method for sequencing a nucleic acid comprising the steps of:
   a) contacting a target nucleic acid with a primer under conditions wherein said primer anneals to said target nucleic acid in a sequence specific manner and wherein at least a portion of said primer is complementary to a portion of said target nucleic acid;
   b) incorporating a hydrocarbyldithiomethyl-modified nucleotide into said primer; and
   c) detecting incorporation of said hydrocarbyldithiomethyl-modified nucleotide, wherein said hydrocarbyldithiomethyl-modified nucleotide is complementary to said target nucleic acid at said hydrocarbyldithiomethyl-modified nucleotide's site of incorporation thereby identifying the sequence of one nucleobase of said target nucleic acid.

2. The method of claim 1 wherein said incorporating step is catalyzed by a DNA polymerase.

3. The method of claim 1 wherein said sequencing method is selected from the group consisting of minisequencing and sequencing by synthesis.

4. The method of claim 1 wherein said method is effective for use with a sequencing array.

5. A method for sequencing a nucleic acid comprising the steps of:

a) contacting a target nucleic acid with a primer under conditions wherein said primer anneals to said target nucleic acid in a sequence specific manner and wherein at least a portion of said primer is complementary to a portion of said target nucleic acid;

b) incorporating a first 3'-hydrocarbyldithiomethyl-modified nucleotide into said primer;

c) detecting said incorporation of said first 3'-hydrocarbyldithiomethyl-modified nucleotide thereby identifying the sequence of a nucleobase of said target nucleic acid;

d) removing said hydrocarbyldithiomethyl group from said first incorporated hydrocarbyldithiomethyl-modified nucleotide to form a first elongated primer having a free hydroxyl group;

e) incorporating a second 3'-hydrocarbyldithiomethyl-modified nucleotide into said first elongated primer; and f) detecting said second hydrocarbyldithiomethyl-modified nucleotide thereby identifying the sequence of another nucleobase of said target nucleic acid, wherein said first 3'-hydrocarbyldithiomethyl-modified nucleotide and said second 3'-hydrocarbyldithiomethyl-modified nucleotide are complementary to said target nucleic acid at each said nucleotide's site of incorporation.

6. The method of claim 5 wherein said detecting steps are performed before removing said hydrocarbyldithiomethyl group.

7. The method of claim 5 wherein said detecting steps are performed after removing said hydrocarbyldithiomethyl group.

8. The method of claim 5 wherein said method is effective for use with a sequencing array.

9. The method of claim 5 wherein steps a), b), c), d), e), and f) are performed under conditions that do not disrupt the annealing of said primer to said target nucleic acid.

10. A method for sequencing a nucleic acid comprising the steps of:

a) providing a primer array comprising a plurality of sequencing primers;

b) contacting a target nucleic acid with said primer array under conditions wherein said sequencing primers anneal to said target nucleic acid in a sequence specific manner thereby forming target-primer complexes between complementary portions of said sequencing primers and said target nucleic acid;

c) incorporating a first 3'-hydrocarbyldithiomethyl-modified nucleotide into at least one sequencing primer portion of said target-primer complexes, said first 3'-hydrocarbyldithiomethyl-modified nucleotide being complementary to said target nucleic acid; and d) detecting said incorporation of said first 3'-hydrocarbyldithiomethyl-modified nucleotide, wherein said first 3'-hydrocarbyldithiomethyl-modified nucleotide is complementary to said target sequence at said first 3'-hydrocarbyldithiomethyl-modified nucleotide's site of incorporation.

11. The method of claim 10 further comprising the steps of:

e) removing said hydrocarbyldithiomethyl group from said first incorporated 3'-hydrocarbyldithiomethyl-modified nucleotide to form a first elongated target-primer complex having a free 3'hydroxyl group;

f) incorporating a second hydrocarbyldithiomethyl-modified nucleotide into said first elongated target-primer complex; and g) detecting said second 3'-hydrocarbyldithiomethyl-modified nucleotide, wherein said second 3'-hydrocarbyldithiomethyl-modified nucleotide is complementary to said target sequence at said second 3'-hydrocarbyldithiomethyl-modified nucleotide's site of incorporation.

12. The method of claim 10 wherein said detecting said incorporation step is performed before removing a hydrocarbyldithiomethyl moiety.

13. The method of claim 10 wherein said method is effective for producing a plurality of nucleotide sequences, said nucleotide sequences corresponding to overlapping nucleotide sequences of said target nucleic acid.

14. The method of claim 11 wherein said step e) is performed under conditions that do not disrupt said target-primer complexes.

* * * * *

UNITED STATES PATENT AND TRADEMARK OFFICE
CERTIFICATE OF CORRECTION

PATENT NO.     : 6,309,836 B1                                    Page 1 of 1
DATED          : October 30, 2001
INVENTOR(S)    : Marek Kwiatkowski It is certified that error appears in the above-identified patent and that said Letters Patent is hereby corrected as shown below:

<u>Title page,</u>
Item [56], References Cited, FOREIGN PATENT DOCUMENTS, please insert the following:

-- WO 91/00868    01/1991
           WO 95/31434    11/1995
           WO 96/23807    08/1996
           WO 98/08857    03/1998
           WO 98/39481    09/1998 --

OTHER PUBLICATIONS, please insert the following:

-- Bonfils and Thuong, <u>Tetrahedron Letters</u>, 1991, 32(26):3053-3056 --

Signed and Sealed this

Twenty-seventh Day of May, 2003

JAMES E. ROGAN
*Director of the United States Patent and Trademark Office*